(12) United States Patent
Shimuta

(10) Patent No.: US 11,464,439 B2
(45) Date of Patent: Oct. 11, 2022

(54) GRIP-TYPE ELECTROCARDIOGRAPHIC MEASURING DEVICE

(71) Applicant: Murata Manufacturing Co., Ltd., Nagaokakyo (JP)

(72) Inventor: Toru Shimuta, Nagaokakyo (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 770 days.

(21) Appl. No.: 16/375,865

(22) Filed: Apr. 5, 2019

(65) Prior Publication Data

US 2019/0231205 A1 Aug. 1, 2019

Related U.S. Application Data

(63) Continuation of application No. PCT/JP2017/033458, filed on Sep. 15, 2017.

(30) Foreign Application Priority Data

Oct. 18, 2016 (JP) .............................. JP2016-204618

(51) Int. Cl.
*A61B 5/26* (2021.01)
*A61B 5/332* (2021.01)
(Continued)

(52) U.S. Cl.
CPC ............ *A61B 5/332* (2021.01); *A61B 5/0245* (2013.01); *A61B 5/02427* (2013.01); *A61B 2562/185* (2013.01)

(58) Field of Classification Search
None
See application file for complete search history.

(56) References Cited

U.S. PATENT DOCUMENTS

2005/0004487 A1* 1/2005 Ishida .................. A61B 5/7445
600/523
2013/0261414 A1 10/2013 Tal et al.
(Continued)

FOREIGN PATENT DOCUMENTS

| CN | 201127603 Y | 10/2008 |
| CN | 103582451 A | 2/2014 |

(Continued)

OTHER PUBLICATIONS

Official Communication issued in corresponding Chinese Patent Application No. 201780064129.0, dated Apr. 2, 2021.
(Continued)

*Primary Examiner* — Yi-Shan Yang
(74) *Attorney, Agent, or Firm* — Keating & Bennett, LLP

(57) ABSTRACT

A grip-type electrocardiographic measuring device includes a main body portion that has a spheroid shape, a plate-shaped flange portion mounted on a side surface of the main body portion, a first electrocardiographic electrode disposed at a back surface side of the main body portion and making contact with one hand when the main body portion is gripped by the one hand, and a second electrocardiographic electrode disposed on a surface of the flange portion and making contact with a finger of the other hand when the flange portion is pinched by the other hand. The flange portion has flexibility and is bendable from a mounting portion on the main body portion.

17 Claims, 7 Drawing Sheets

(51) Int. Cl.
  *A61B 5/024* (2006.01)
  *A61B 5/0245* (2006.01)

(56) References Cited

U.S. PATENT DOCUMENTS

| | | | |
|---|---|---|---|
| 2013/0281868 A1 | 10/2013 | Kawachi et al. | |
| 2014/0088396 A1 | 3/2014 | Shimuta | |
| 2015/0201876 A1* | 7/2015 | Zhou ...................... | A61B 5/332 |
| | | | 600/324 |
| 2018/0064355 A1* | 3/2018 | Shimuta ............... | A61B 5/6826 |

FOREIGN PATENT DOCUMENTS

| | | |
|---|---|---|
| JP | 03-91304 U | 9/1991 |
| JP | 03-91306 U | 9/1991 |
| JP | 09-173304 A | 7/1997 |
| JP | 2005-000468 A | 1/2005 |
| JP | 2007-319256 A | 12/2007 |
| JP | 2013-226189 A | 11/2013 |
| WO | 2016/181808 A1 | 11/2016 |

OTHER PUBLICATIONS

Official Communication issued in International Patent Application No. PCT/JP2017/033458 dated Nov. 14, 2017.

\* cited by examiner

US 11,464,439 B2

GRIP-TYPE ELECTROCARDIOGRAPHIC MEASURING DEVICE

CROSS REFERENCE TO RELATED APPLICATIONS

This application claims the benefit of priority to Japanese Patent Application No. 2016-204618 filed on Oct. 18, 2016 and is a Continuation Application of PCT Application No. PCT/JP2017/033458 filed on Sep. 15, 2017. The entire contents of each of these applications are hereby incorporated herein by reference.

BACKGROUND OF THE INVENTION

1. Field of the Invention

The present invention relates to a grip-type electrocardiographic measuring device that acquires an electrocardiographic signal.

2. Description of the Related Art

In recent years, there has been increasing interest in management, maintenance, and enhancement of health. It has therefore been desired that people are able to more easily obtain biological information, such as pulse and electrocardiogram information, in everyday life. Japanese Unexamined Patent Application Publication No. 9-173304 discloses an electrocardiographic measuring device (an adapter for managing a biological risk) that acquires electrocardiographic signals from palms and fingers of both hands.

More specifically, the device disclosed in Japanese Unexamined Patent Application Publication No. 9-173304 (the adapter for managing the biological risk) includes a sensor unit and a modem. The sensor unit includes a flexible rod in which a negative electrode (−) and a thermistor are provided at a tip portion thereof. On the other hand, an antibacterial case of the modem includes a neutral electrode (N), a positive electrode (+), a finger cuff, and the like.

A body temperature is measured by the thermistor, and the electrocardiogram and heartbeat are measured with three poles, i.e., the negative electrode (−), the neutral electrode, and the positive electrode (+), and blood pressure and oxygen saturation are measured with the finger cuff. In addition, the antibacterial case of the modem is provided with a housing portion that allows the flexible rod to be pulled out in a telescopic manner. In other words, the flexible rod is housed in the housing portion provided in the antibacterial case of the modem, so that the flexible rod can be pulled out in the telescopic manner.

As described above, the device disclosed in Japanese Unexamined Patent Application Publication No. 9-173304 is configured such that the negative electrode (−) provided at the tip of the flexible rod is held (or pinched) by one hand, the antibacterial case of the modem is held (gripped) by the other hand, and the other hand makes contact with the neutral electrode (N) and the positive electrode (+) provided on the antibacterial case of the modem, thus acquiring an electrocardiographic signal (electrocardiographic measurement).

An unnatural gripping method tenses muscles of the hand in the electrocardiographic measurement. When, in particular, the electrocardiographic measurement is performed continuously for equal to or longer than several minutes, myoelectric noise or noise generated by slippage of skin and the electrode may be mixed in the electrocardiographic signal. However, the device disclosed in Japanese Unexamined Patent Application Publication No. 9-173304 does not take ease of gripping in terms of a shape thereof into consideration. In particular, since the negative electrode (−) is provided on the tip portion of the flexible rod, for example, when the thin flexible rod is pinched by fingers, a lot of myoelectric noise, the noise generated by the slippage of the skin and the electrode, and other noise may be mixed in the electrocardiographic signal.

In addition, in the device disclosed in Japanese Unexamined Patent Application Publication No. 9-173304, although the sensor unit (flexible rod) may be housed in the housing portion of the antibacterial case of the modem in the telescopic manner, a space for accommodating the flexible rod and a housing mechanism thereof is required, resulting in a problem that the size of the antibacterial case of the modem is increased.

SUMMARY OF THE INVENTION

Preferred embodiments of the present invention provide grip-type electrocardiographic measuring devices that each acquire an electrocardiographic signal from both hands, which reduce or prevent a user from feeling fatigue even if the user holds electrocardiographic electrodes for a long time, are able to stably measure the electrocardiographic signal for a long time, and are excellent in a housing property of the electrocardiographic electrode.

A grip-type electrocardiographic measuring device according to a preferred embodiment of the present invention includes a main body portion that has a spheroid or substantially spheroid shape, a plate-shaped flange portion that is mounted on a side surface of the main body portion, a first electrocardiographic electrode that is disposed on the main body portion and makes contact with one hand when the main body portion is gripped by the one hand, and a second electrocardiographic electrode that is disposed on a surface of the flange portion and makes contact with a finger of the other hand when the flange portion is pinched by the other hand, wherein the flange portion has flexibility and is bendable from a mounting portion on the main body portion.

With the grip-type electrocardiographic measuring device described above, when a user holds the device with both hands, the user grips the main body portion having the spheroid or substantially spheroid shape by the one hand (a thumb and the other four fingers) and pinches (clamps) the plate-shaped flange portion by the fingers (for example, a thumb and an index finger) of the other hand. Therefore, both hands support each other, and the user does not experience fatigue even if the user maintains the posture for a long time (for example, several minutes). Further, the flange portion has flexibility and is bendable from the mounting portion on the main body portion. Therefore, by bending (deforming) the flange portion protruding (projecting) from the main body portion, the flange portion is able to be easily housed and the device is able to be easily carried. As a result, it is possible to provide a grip-type electrocardiographic measuring device which reduces or prevents the user from feeling fatigue even if the user holds the electrocardiographic electrodes for a long time, is able to stably measure the electrocardiographic signal for a long time, and is excellent in a housing property of the electrocardiographic electrodes.

It is preferable that the grip-type electrocardiographic measuring device includes a mechanism which prevents the flange portion from hanging down toward a back surface side of the main body portion during measurement.

In this case, the flange portion is structured so as not to hang down toward the back surface side of the main body portion. Therefore, it is possible to prevent the flange portion from hanging down and being difficult to be pinched by the fingers during measurement. Furthermore, it is not necessary to support the flange portion with the fingers so as not to hang down during measurement, and it is therefore possible to reduce or prevent electromyogram noise, noise generated by slippage of skin and the electrode, and other noise from being mixed in the electrocardiographic signal even with, for example, continuous measurement of equal to or longer than several minutes.

In addition, it is preferable that the grip-type electrocardiographic measuring device include a fixing member which fixes the flange portion along an outer peripheral surface of the main body portion in the housing.

In this case, the flange portion is able to be fixed (i.e., fixed in a closed state) along the outer peripheral surface of the main body portion while the device is not used. Therefore, it is possible to easily house the flange portion and prevent the flange portion from being broken with repeated bending thereof due to vibration or other forces while, for example, the device is carried.

In a grip-type electrocardiographic measuring device according to a preferred embodiment of the present invention, it is preferable that the second electrocardiographic electrode is disposed on the flange portion so as to be exposed to an outer surface of the flange portion in a state in which the flange portion is fixed along the outer peripheral surface of the main body portion.

In this case, the second electrocardiographic electrode is structured so as to be exposed to an outer side portion in the state in which the flange portion is fixed along the outer peripheral surface of the main body portion. Therefore, in addition to the method of acquiring (measuring) the electrocardiographic signal by both hands by opening the flange portion, the electrocardiographic signal is able to be measured by gripping the main body portion and pressing the second electrocardiographic electrode against biological skin (e.g., chest or other suitable location) in the closed state of the flange portion. Accordingly, even when an amplitude of the electrocardiographic signal is small between both hands (i.e., lead I), it is possible to acquire (measure) the electrocardiographic signal having a larger amplitude between the hand and the chest or other suitable location.

It is preferable that the grip-type electrocardiographic measuring device includes a stopper portion which projects along an axial direction of the main body portion and abuts against a side surface of a thumb of one hand to restrict a position of the thumb when a user grips the main body portion by the one hand, wherein the flange portion is mounted so as to be bendable in a direction which is orthogonal or substantially orthogonal to a projecting direction of the stopper portion.

When the user holds the device with both hands, the finger (e.g., the index finger and/or the middle finger and/or the thumb) of the one hand makes contact with the first electrocardiographic electrode disposed on the main body portion, and the finger (e.g., the thumb and/or the index finger) of the other hand makes contact with the second electrocardiographic electrode disposed on the surface of the flange portion. In this case, the position of the thumb of the one hand is restricted by the stopper portion projecting along the axial direction of the main body portion, and the plate-shaped flange portion is mounted on the side surface of the main body portion so as to be bendable in the direction (up to an angle) which is orthogonal or substantially orthogonal to the projecting direction of the stopper portion, so that both hands are able to be prevented from making contact with each other. That is, the user is able to hold the device without contact between both hands. Further, even when the main body portion is miniaturized, it is able to be easily gripped while the fingers of both hands do not interfere with each other. In addition, since the fingers of both hands hardly make contact with each other, it is possible to prevent deterioration in S/N due to contact between the fingers.

Preferred embodiments of the present invention provide grip-type electrocardiographic measuring devices that each acquire an electrocardiographic signal from both hands, which reduce or prevent a user from feeling fatigue even if the user holds electrocardiographic electrodes for a long time, are able to stably measure the electrocardiographic signal for a long time, and are excellent in a housing property of the electrocardiographic electrode.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 1:
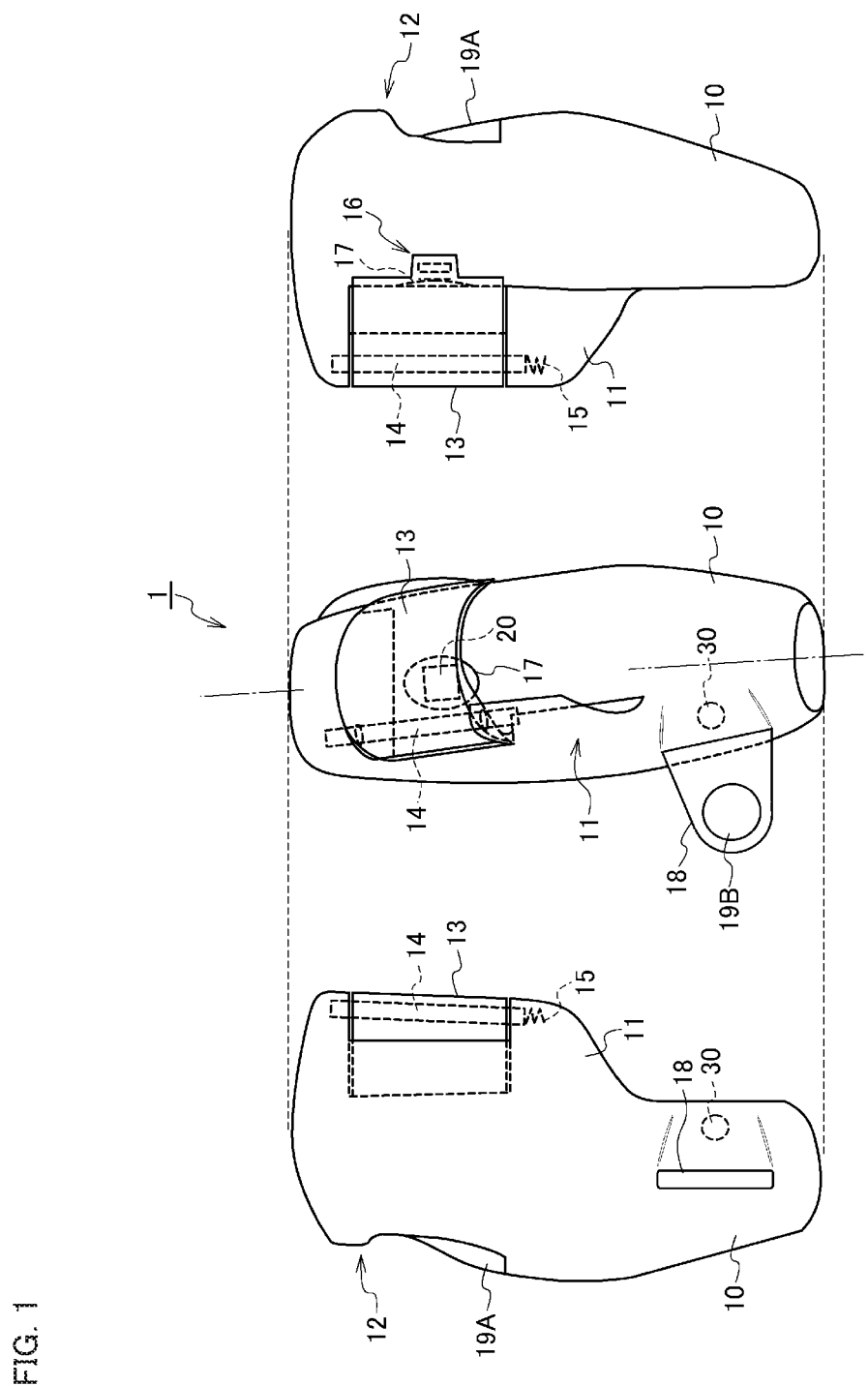
FIG. 1 illustrates a front view and right and left side views (a state in which a flange portion is opened) of a grip-type electrocardiographic measuring device according to a preferred embodiment of the present invention.

Hereinafter, preferred embodiments of the present invention will be described in detail with reference to the accompanying drawings. In the drawings, the same or corresponding portions and elements are denoted by the same reference numerals. In addition, in each of the drawings, the same or similar elements are denoted by the same reference numerals, and overlapped description thereof will be omitted.

Figure 2:
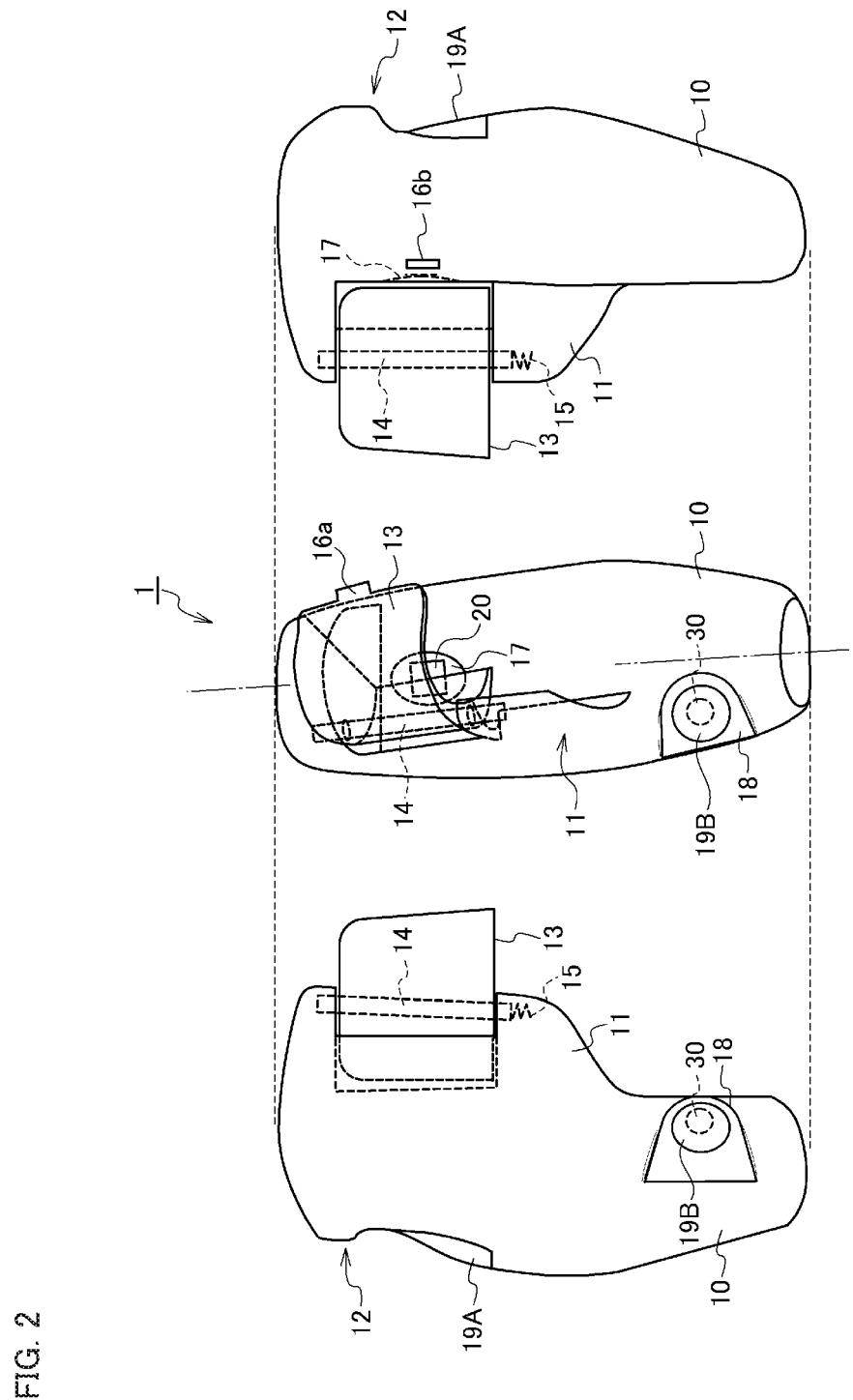
FIG. 2 illustrates a front view and right and left side views (a state in which the flange portion is closed) of a grip-type electrocardiographic measuring device according to a preferred embodiment of the present invention.
Figure 3:
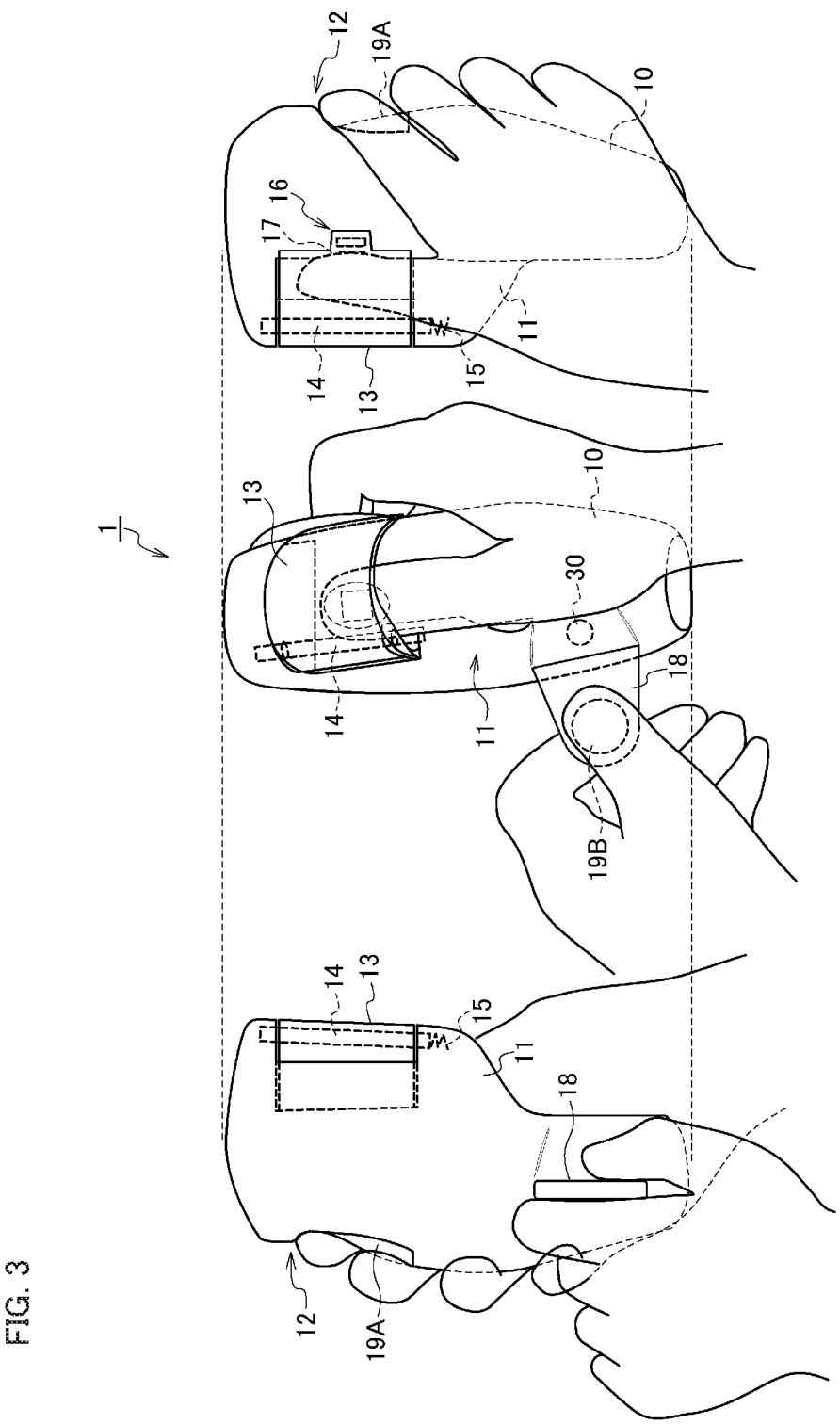
FIG. 3 is a view illustrating a state (a state in measurement) in which a grip-type electrocardiographic measuring device according to a preferred embodiment of the present invention is gripped by hands.
Figure 4:
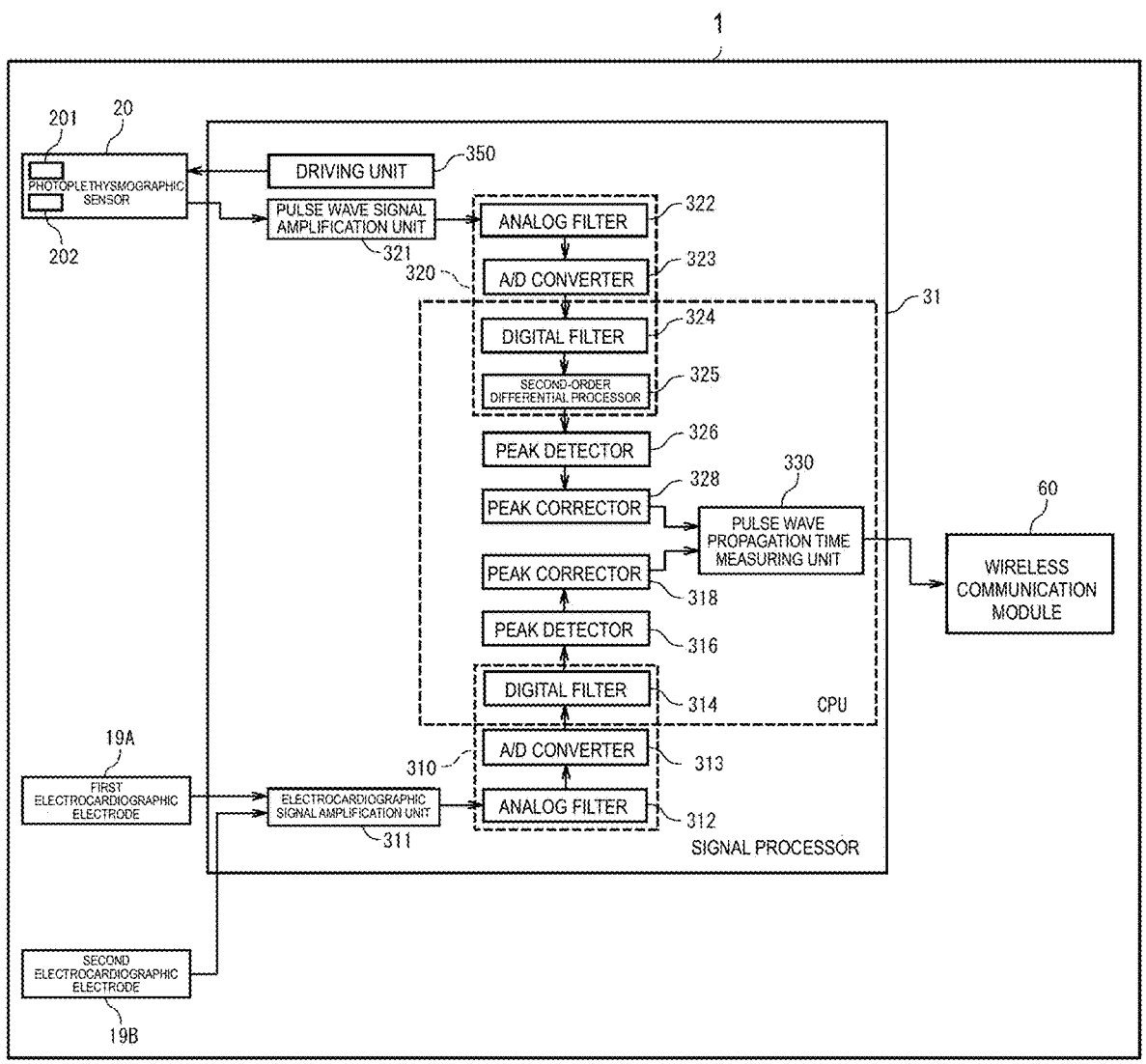
FIG. 4 is a block diagram illustrating the functional configuration of a grip-type electrocardiographic measuring device according to a preferred embodiment of the present invention.

First, the configuration of a grip-type electrocardiographic measuring device 1 according to a preferred embodiment of the present invention will be described with reference to FIG. 1 to FIG. 4. FIG. 1 illustrates a front view and right and left side views (a state in which a flange portion is opened) of the grip-type electrocardiographic measuring device 1 according to the present preferred embodiment, and FIG. 2 illustrates a front view and right and left side views (a state in which the flange portion 18 is closed) of the grip-type electrocardiographic measuring device 1. FIG. 3 is a view illustrating a state (a state in measurement) in which the grip-type electrocardiographic measuring device 1 is gripped by hands. FIG. 4 is a block diagram illustrating the functional configuration of the grip-type electrocardiographic measuring device 1.

The grip-type electrocardiographic measuring device 1 is capable of acquiring an electrocardiographic signal and a photoplethysmographic signal and measuring a heart rate, a pulse rate, a pulse wave propagation time, and other parameters by being gripped by a user.

The grip-type electrocardiographic measuring device 1 includes a main body portion 10 which has a spheroid or substantially spheroid shape that the user grips by a thumb and the other four fingers of one hand (for example, the right hand) during measurement. In the main body portion 10, a stopper portion (locking portion) 11, which abuts against a side surface of a middle joint and/or a base joint of the thumb of the one hand to restrict (stop) a position of the thumb when the user grips the main body portion 10 by the one hand, projects along the axial direction (see a dashed-dotted line in FIGS. 1 and 2) of the main body portion 10. It is preferable that the main body portion 10 is made of, for example, resin or other suitable material. Also, the "substantially spheroid shape" is intended not to be limited to the spheroid in a strict sense defined by geometry.

As seen from the stopper portion 11 side, a step 12 (protrusion) to guide an index finger of the one hand to an appropriate grip position when the user grips the grip-type electrocardiographic measuring device 1 is provided in the main body portion 10 at a position closer to a tip portion than the center at the back surface side. In other words, when the user grips the device with an index finger along the step 12, the positions of the respective fingers are fixed or substantially fixed, and variations in the position of the finger tip of the thumb in the vertical direction are able to be reduced or prevented.

The plate-shaped flange portion 18 is mounted on the side surface of the main body portion 10 (the side surface at which the stopper portion 11 projects). The flange portion 18 has flexibility and is bendable from a mounting portion on the main body portion 10. For example, the flange portion 18 is structured so as to be bent and opened (unfolded) up to a direction (an angle) which is orthogonal or substantially orthogonal to a projecting direction of the stopper portion 11. The flange portion 18 is bent and opened (unfolded) in the direction which is orthogonal or substantially orthogonal to the projecting direction of the stopper portion 11 during measurement, thus preventing the finger tip of the thumb of the hand (for example, the right hand) gripping the main body portion 10 from making contact with fingers of a hand (for example, the left hand) holding the flange portion 18.

As a material of the flange portion 18, an electrode material (details thereof will be described later) that is used for a second electrocardiographic electrode 19B, which will be described later, may preferably be used. Alternatively, for example, the configuration in which a non-conductive (insulating) rubber, film, cloth, or other material is used as a base material, the second electrocardiographic electrode 19B is fixed to a surface of the base material, and a cable for connecting the second electrocardiographic electrode 19B and an electrocardiographic input terminal (not illustrated) of the main body portion 10 is inserted through the base material may be provided. The flange portion 18 is preferably structured such that the thickness of an outer edge is larger than the thickness of an inner side portion (central portion).

Further, after completion of the measurement, the flange portion 18 is able to be bent and closed to be housed along the outer peripheral surface of the main body portion 10. Further, it is preferable that a fixing member (a fixing mechanism) which fixes (locks) the flange portion 18 along the outer peripheral surface of the main body portion 10 during housing is provided (i.e., the flange portion 18 is able to be fixed along the outer periphery of the main body portion 10). More specifically, for example, it is preferable that a magnet 30 is attached respectively to (or either one of) the main body portion 10 and the flange portion 18 and the flange portion 18 is fixed with magnetic force of the magnet (s) 30. Alternatively, a protrusion (or a recess) may be provided on the main body portion 10, a recess/hole (or a projection) may be provided in the flange portion 18 so as to be fitted with the protrusion (or the recess), and the flange portion 18 may be fixed by fitting the recess/hole (or the projection) provided in the flange portion 18 with the protrusion (or the recess) provided on the main body portion 10.

It is preferable that a concave portion (which is able to house therein the flange portion 18) corresponding to the thickness of the flange portion 18 is provided in an area of the outer peripheral surface of the main body portion 10 in which the flange portion 18 is housed so as to prevent the flange portion 18 from protruding greatly from the main body portion 10 when the flange portion 18 is fixed along the outer peripheral surface of the main body portion 10. In addition, it is preferable that the flange portion 18 is able to be fixed with no deflection in the flange portion 18 when being fixed. This is because if the flange portion 18 is deflected, the flange portion 18 is easily broken when vibration or pressure is applied thereto while the device is carried. Further, since the flange portion 18 also electrically connects the second electrocardiographic electrode 19B and the main body portion 10, noise tends to be mixed by influences of vibration, body movement, and other forces when the flange portion is in the deflected state.

As described above, since the flange portion 18 has flexibility and is bendable, it is preferable that a mechanism (stopper mechanism) which prevents the flange portion 18 from hanging down (bending) toward the back surface side of the main body portion 10 in measurement is provided. More specifically, for example, it is possible to achieve the stopper function by providing, for example, a projecting stopper (flange stopper) to prevent the flange portion 18 from hanging down toward the back surface side of the main body portion 10 at the back surface side of a connecting portion between the flange portion 18 and the main body portion 10. Alternatively, the flange portion 18 itself may be structured so as not to be bent toward the back surface side of the main body portion 10. For example, by bonding ends of two films having different lengths while making the shorter film with a less stretchable material (than the longer film), the flange portion 18 is able to be bent to the shorter film side and to hardly be bent to the longer film side.

A first electrocardiographic electrode 19A is disposed at the back surface side of the main body portion 10 at a position closer to a base end portion relative to the step 12 (protrusion). That is, the first electrocardiographic electrode 19A is disposed such that when the user grips the main body portion 10 by the one hand (for example, the right hand), the finger (for example, the index finger and/or the middle finger) of the one hand makes contact therewith.

On the other hand, the second electrocardiographic electrode 19B preferably having a circular or substantially circular shape, for example, to detect the electrocardiographic signal is disposed on the surface (or the surfaces at the back surface side and the front surface side) of the flange portion 18 at the back surface side (i.e., the side exposed to the outside when the flange portion 18 is closed). That is, the second electrocardiographic electrode 19B is disposed such that when the user pinches (clamps) the flange portion 18 with fingers (for example, a thumb and an index finger) of the other hand (for example, the left hand), the finger (for example, the thumb and/or the index finger) of the other hand makes contact therewith.

In other words, when the user grips the main body portion 10 and the flange portion 18 of the grip-type electrocardiographic measuring device 1, the first electrocardiographic electrode 19A and the second electrocardiographic electrode 19B acquire the electrocardiographic signal corresponding to potential difference between the right and left hands of the user with contact between the right and left hands (finger tips) of the user and them. As an electrode material of the first electrocardiographic electrode 19A and the second electrocardiographic electrode 19B, for example, metal (which is highly resistant to corrosion and gives less metallic allergy, such as stainless steel, titanium, or Au, for example), conductive gel, conductive rubber, conductive cloth, or other suitable material is preferably used. Alternatively, for example, conductive plastic, a capacitive coupling electrode, or other suitable material may also be used as the electrode material of the first electrocardiographic electrode 19A and the second electrocardiographic electrode 19B. Each of the first electrocardiographic electrode 19A and the second electrocardiographic electrode 19B is connected to a signal processor 31, which will be described later, with a cable, and outputs the electrocardiographic signal to the signal processor 31 with the cable interposed therebetween.

As described above, the second electrocardiographic electrode 19B is disposed on the flange portion 18 so as to be exposed to the outer side portion (surface side) of the main body portion 10 (flange portion 18) at least in the state in which the flange portion 18 is fixed along the outer peripheral surface of the main body portion 10. In other words, the second electrocardiographic electrode 19B may be disposed only on the back surface of the flange portion 18, or may be disposed on each of the back surface and the front surface thereof. Therefore, it is also possible to measure the electrocardiographic signal by gripping the main body portion 10 in the state in which the flange portion 18 is fixed (housed) along the outer periphery of the main body portion 10 and pressing the second electrocardiographic electrode 19B exposed to the outer side portion against the skin (for example, chest or other suitable location) of the living body.

Further, a light shielding cover (light shielding member) 13 providing a light shielding function and shielding light so as to prevent disturbance light from entering a photoplethysmographic sensor 20, which will be described later, during measurement is mounted on the main body portion 10 in an openable/closable manner by swinging in the peripheral direction of the main body portion 10. The light shielding cover 13 preferably has a semi-cylindrical or substantially semi-cylindrical shape (curved planar shape) so as to cover a user's thumb during measurement.

More specifically, the light shielding cover 13 is mounted on the main body portion 10 at the tip side of the stopper portion 11 (the main body portion 10) along the stopper portion 11 of the main body portion 10 so as to be swingable about a swing shaft 14 provided in parallel or substantially in parallel or substantially in parallel to the axial direction of the main body portion 10. More specifically, the light shielding cover 13 is mounted so as to swing such that when seen from a base end portion side of the main body portion 10, one end portion (end side) thereof protrudes toward the photoplethysmographic sensor 20 side relative to the stopper portion 11 in an opened state, and the one end portion (end side) thereof is flush or substantially flush with the end surface of the stopper 11 in a closed state.

Further, a biasing member 15, such as a spring, which biases the light shielding cover 13 in the open direction is preferably included in the swing shaft 14 of the light shielding cover 13. Therefore, the light shielding cover 13 is opened automatically when the lock is released (details of which will be described later) and the user does not grip the main body 10. The light shielding cover 13 swings and is closed so as to cover the finger tip of the thumb with an operation of moving the user's thumb until the thumb abuts against the stopper portion 11 when the user grips the main body portion 10.

Further, the light shielding cover 13 includes a lock mechanism 16 which locks (fixes) the light shielding cover 13 in the closed state, for example, when not in use. More specifically, a claw portion 16*a* is provided on one end portion (end side) of the light shielding cover 13 and a groove portion 16*b* into which the claw portion 16*a* is fitted is provided in the side surface of the main body portion 10. The claw portion 16*a* provided on the end portion of the light shielding cover 13 is fitted into the groove portion 16*b*, so that the light shielding cover 13 is fixed (locked) to the main body portion 10.

The photoplethysmographic sensor 20 is disposed on the main body portion 10 at a position (a position on the center line of the main body portion 10) which is offset from the swing shaft 14 of the light shielding cover 13 along the peripheral direction of the main body portion 10. The photoplethysmographic sensor 20 includes a light emitting element 201 and a light receiving element 202, and acquires a photoplethysmographic signal from the finger tip of the thumb restricted by the stopper portion 11. The photoplethysmographic sensor 20 optically detects the photoplethysmographic signal by utilizing absorption characteristics of hemoglobin in blood.

Here, in the main body portion 10, an area in which the photoplethysmographic sensor 20 including the light emitting element 201 and the light receiving element 202 is disposed is recessed in an elliptical or substantially elliptical shape from the peripheral surface. In other words, the photoplethysmographic sensor 20 is disposed at the center or approximate center of a recess 17 provided in the main body portion 10. The user is therefore able to reliably locate the finger tip of the thumb on the photoplethysmographic sensor 20 without viewing by placing an inner portion of the thumb on the recess 17.

As illustrated in FIG. 4, the light emitting element 201 emits light in response to a pulse driving signal output from a driver 350 of the signal processor 31 to be described later. As the light emitting element 201, for example, an LED, a VCSEL (Vertical Cavity Surface Emitting Laser), a resonator LED, or other suitable light emitting element may preferably be used. Note that the driver 350 generates and outputs the pulse driving signal which drives the light emitting element 201.

The light receiving element 202 outputs a detection signal corresponding to the intensity of light that is emitted from the light emitting element 201, passes through the thumb or is reflected by the thumb, and is incident thereon. As the light receiving element 202, for example, a photodiode, a phototransistor, or other suitable light receiving element may preferably be used. In the present preferred embodiment, a photodiode is used as the light receiving element 202.

The light receiving element 202 is connected to the signal processor 31, and the detection signal (photoplethysmographic signal) obtained by the light receiving element 202 is output to the signal processor 31.

In this case, the main body portion 10 accommodates therein the signal processor 31 and a wireless communication module 60 that transmits biological information, such as the measured electrocardiographic signal, photoplethysmographic signal, and pulse wave propagation time, to an external device. In addition, the main body portion 10 accommodates therein a battery (not illustrated) that supplies electric power to the photoplethysmographic sensor 20, the signal processor 31, the wireless communication module 60, and other components.

Each of the pair of electrocardiographic electrodes (the first electrocardiographic electrode 19A and the second electrocardiographic electrode 19B) and the photoplethysmographic sensor 20 is connected to the signal processor 31, and the detected electrocardiographic signal and photoplethysmographic signal are input to the signal processor 31.

The signal processor 31 measures the pulse wave propagation time from a time difference between R wave peaks of the detected electrocardiographic signal and rising points (peaks) of the photoplethysmographic signal (or acceleration pulse waves). Further, the signal processor 31 processes the input electrocardiographic signal and measures a heart rate, a heartbeat interval, and other parameters. Moreover, the signal processor 31 processes the input photoplethysmographic signal and measures a pulse rate, a pulse interval, and other parameters.

The signal processor 31 includes amplifiers 311 and 321, a first signal processor 310, a second signal processor 320, peak detectors 316 and 326, peak correctors 318 and 328, and a pulse wave propagation time measurer 330. Further, the first signal processor 310 includes an analog filter 312, an A/D converter 313, and a digital filter 314. On the other hand, the second signal processor 320 includes an analog filter 322, an A/D converter 323, a digital filter 324, and a second-order differential processor 325.

In the above-described elements, the digital filters 314 and 324, the second-order differential processor 325, the peak detectors 316 and 326, the peak correctors 318 and 328, and the pulse wave propagation time measurer 330 are preferably defined by a CPU to perform arithmetic processing, a ROM to store a program and data to cause the CPU to execute pieces of processing, a RAM to temporarily store various pieces of data, such as an arithmetic result, for example. In other words, the CPU executes the program stored in the ROM to implement the functions of the units described above.

The amplifier 311 is preferably defined by, for example, an operational amplifier or other suitable amplifier and amplifies the electrocardiographic signal detected by the pair of electrocardiographic electrodes (the first electrocardiographic electrode 19A and the second electrocardiographic electrode 19B). The electrocardiographic signal amplified by the amplifier 311 is output to the first signal processor 310. Similarly, the amplifier 321 is preferably defined by, for example, an operational amplifier or other suitable amplifier and amplifies the photoplethysmographic signal detected by the photoplethysmographic sensor 20. The photoplethysmographic signal amplified by the amplifier 321 is output to the second signal processor 320.

As described above, the first signal processor 310 includes the analog filter 312, the A/D converter 313, and the digital filter 314, and extracts a pulsation component by performing filtering processing on the electrocardiographic signal amplified by the amplifier 311.

Further, as described above, the second signal processor 320 includes the analog filter 322, the A/D converter 323, the digital filter 324, and the second-order differential processor 325, and extracts a pulse component by performing filtering processing and second-order differential processing on the photoplethysmographic signal amplified by the amplifier 321.

The analog filters 312 and 322 and the digital filters 314 and 324 perform filtering to remove components (noise) other than frequencies characterizing the electrocardiographic signal and the photoplethysmographic signal and improve S/N. More specifically, frequency components of about 0.1 Hz to about 200 Hz, for example, are dominant for the electrocardiographic signal and frequency components of about 0.1 Hz to about several tens of Hz are dominant for the photoplethysmographic signal. Therefore, the digital filters 314 and 324 and the analog filters 312 and 322, such as low pass filters and band pass filters, are used to perform the filtering processing thereon and selectively transmit only signals in the above-described frequency ranges, so that the S/N is improved.

In addition, when only extraction of the pulsation component is intended (i.e., when it is not necessary to obtain a waveform, for example), a passing frequency range may be narrowed to exclude components other than the pulsation component in order to improve noise resistance. In addition, both of the analog filters 312 and 322 and the digital filters 314 and 324 need not be necessarily provided, and only one of the analog filters 312 and 322 and the digital filters 314 and 324 may be provided. The electrocardiogram signal that has been subjected to the filtering processing by the analog filter 312 and the digital filter 314 is output to the peak detector 316. Similarly, the photoplethysmographic signal that has been subjected to the filtering processing by the analog filter 322 and the digital filter 324 is output to the second-order differential processor 325.

The second-order differential processor 325 acquires second-order differential pulse waves (acceleration pulse waves) by performing second-order differentiation on the photoplethysmographic signal. The acquired acceleration pulse waves are output to the peak detector 326. Since the rising points of the photoplethysmographic waves are not clear and are not easily detected in some cases, it is preferable that the peak detection be performed after converting the photoplethysmographic waves into the acceleration pulse waves. It is however not essential to provide the second-order differential processor 325, and the second-order differential processor 325 may be omitted.

The peak detector 316 detects the peaks (R waves) of the electrocardiographic signal that have been subjected to the signal processing by the first signal processor 310 (from which the pulsation component has been extracted). On the other hand, the peak detector 326 detects the peaks of the photoplethysmographic signal (acceleration pulse waves)

that have been subjected to the filtering processing by the second signal processor 320. Note that the peak detector 316 and the peak detector 326 perform the peak detection within normal ranges of the heartbeat interval and the pulse interval and store pieces of information, such as the peak time and the peak amplitude, in the RAM or other suitable memory for each of the detected peaks.

The peak corrector 318 obtains a delay time of the electrocardiographic signal in the first signal processor 310 (the analog filter 312, the A/D converter 313, and the digital filter 314). The peak corrector 318 corrects the peaks of the electrocardiographic signal, which have been detected by the peak detector 316, based on the obtained delay time of the electrocardiographic signal. Similarly, the peak corrector 328 obtains a delay time of the photoplethysmographic signal in the second signal processor 320 (the analog filter 322, the A/D converter 323, the digital filter 324, and the second-order differential processor 325). The peak corrector 328 corrects the peaks of the photoplethysmographic signal (acceleration pulse waves), which have been detected by the peak detector 326, based on the obtained delay time of the photoplethysmographic signal. The corrected peaks of the electrocardiographic signal and the corrected peaks of the photoplethysmographic signal (acceleration pulse waves) are output to the pulse wave propagation time measurer 330. It is not essential to provide the peak corrector 318, and the peak corrector 318 may be omitted.

The pulse wave propagation time measurer 330 obtains the pulse wave propagation time from the interval (time difference) between the R wave peaks of the electrocardiographic signal, which have been corrected by the peak corrector 318, and the peaks of the photoplethysmographic signal (acceleration pulse waves), which have been corrected by the peak corrector 328.

In addition to the pulse wave propagation time, the pulse wave propagation time measurer 330 also calculates, for example, the heart rate, the heartbeat interval, the heartbeat interval change rate, and other parameters from the electrocardiographic signal. Similarly, the pulse wave propagation time measurer 330 also calculates the pulse rate, the pulse interval, the pulse interval change rate, and other parameters from the photoplethysmographic signal (acceleration pulse wave).

Note that the pieces of acquired measurement data, such as the pulse wave propagation time, the heart rate, and the pulse rate are transmitted to, for example, a PC, a portable music player including a display, a smartphone, or other suitable device with the wireless communication module 60 interposed therebetween. In this case, in addition to the measurement results and the detection results, data, such as measurement date and time, are preferably transmitted.

Next, a non-limiting example of a method of using the grip-type electrocardiographic measuring device 1 will be described. When this grip-type electrocardiographic measuring device 1 is used to detect the electrocardiographic signal and the photoplethysmographic signal and measure the heart rate, the pulse rate, the pulse wave propagation time, and other parameters, as illustrated in FIG. 3, the user grips the main body portion 10 of the grip-type electrocardiographic measuring device 1 by the thumb and the other four fingers of one hand (for example, the right hand). This gripping causes the finger (e.g., the index finger and/or the middle finger) of the one hand to make contact with the first electrocardiographic electrode 19A.

In this case, as described above, when the lock is released and the user does not grip the main body portion 10, the light shielding cover 13 is automatically opened, so that the user is able to naturally grip the main body portion 10. When the user grips the main body portion 10 by the one hand, the user moves the thumb of the one hand until the thumb abuts against the stopper portion 11 (from right to left in the example of FIG. 3), such that the light shielding cover 13 swings and is closed so as to cover the finger tip of the thumb while the end portion (end side) of the light shielding cover 13 is pushed by the thumb. Then, the finger tip of the thumb makes contact with the photoplethysmographic sensor 20 by placing the inner portion of the thumb on the recess 17.

With the other hand (for example, the left hand), the housed flange portion 18 is bent and opened at an angle which is orthogonal or substantially orthogonal to the projecting direction of the stopper portion 11. Then, the user pinches (clamps) the flange portion 18 by the thumb and the index finger of the other hand (for example, the left hand). The finger (the thumb and/or the index finger) of the other hand thus makes contact with the second electrocardiographic electrode 19B.

With the above-described process, the electrocardiographic signal is acquired by the pair of electrocardiographic electrodes (the first electrocardiographic electrode 19A and the second electrocardiographic electrode 19B), and at the same time, the photoplethysmographic signal is acquired by the photoplethysmographic sensor 20. Further, the signal processor 31 acquires the pulse wave propagation time and other parameters from the peak time difference between the electrocardiographic signal and the photoplethysmographic signal. The method of acquiring the pulse wave propagation time and other parameters is as described above, and detailed description thereof will therefore be omitted here.

In this manner, the user is able to detect and measure the electrocardiographic signal, the photoplethysmographic signal, the pulse wave propagation time, and other parameters only by holding the grip-type electrocardiographic measuring device 1 with both hands. Note that the pieces of biological information, such as the electrocardiographic signal, the photoplethysmographic signal, and the pulse wave propagation time, which have been detected or measured, are transmitted to the external device with the wireless communication module 60 interposed therebetween. Thereafter (after the measurement), the flange portion 18 is closed (bent toward the main body portion 10 side), and is housed. At this time, the flange portion 18 is locked (fixed) along the outer peripheral surface (side surface) of the main body portion 10.

As described in detail above, according to the present preferred embodiment, when the user holds the grip-type electrocardiographic measuring device 1 with both hands, the user grips the main body portion 10 having the spheroid or substantially spheroid shape by the one hand (the thumb and the other four fingers) and pinches (clamps) the plate-shaped flange portion 18 by the fingers (for example, the thumb and the index finger) of the other hand. Therefore, both of the hands support each other, and the user hardly feels fatigue even if the user maintains the posture for a long time (for example, several minutes). Further, the flange portion 18 has flexibility and is bendable from the mounting portion on the main body portion 10. Therefore, by bending (deforming) the flange portion 18 protruding (projecting) from the main body portion 10, the flange portion 18 is able to be easily housed and the device is able to be easily carried. As a result, it is possible to provide the grip-type electrocardiographic measuring device 1 which reduces or prevents the user from feeling fatigue even if the user holds the electrocardiographic electrodes 19A and 19B for a long time, is able to stably measure the electrocardiographic signal for a long time, and is excellent in the housing property and portability of the second electrocardiographic electrode 19B (the flange portion 18).

According to the present preferred embodiment, the flange portion 18 is structured so as not to hang down toward the back surface side of the main body portion 10. Therefore, it is possible to prevent the flange portion 18 from hanging down and being difficult to be pinched by the fingers during measurement. Furthermore, it is not necessary to support the flange portion 18 with the fingers so as not to hang down during measurement and it is therefore possible to reduce or prevent electromyogram noise, noise generated by slippage of skin and the electrode, for example, from being mixed in the electrocardiographic signal even with, for example, continuous measurement of equal to or longer than several minutes.

According to the present preferred embodiment, the flange portion 18 is able to be fixed along the outer peripheral surface of the main body portion 10. Therefore, it is possible to easily house the flange portion 18 and prevent the flange portion 18 from being broken with repeated bending thereof due to vibration or other forces while, for example, it is carried.

According to the present preferred embodiment, the second electrocardiographic electrode 19B is exposed to the outer side portion in the state in which the flange portion 18 is fixed along the outer peripheral surface of the main body 10. Therefore, in addition to the method of acquiring (measuring) the electrocardiographic signal with both hands by opening the flange portion 18, the electrocardiographic signal is able to be measured by gripping the main body 10 and pressing the second electrocardiographic electrode 19B against the biological skin (e.g., the chest or other suitable location) in the closed state of the flange portion 18. Accordingly, even when an amplitude of the electrocardiographic signal is small between both hands (i.e., lead I), it is possible to acquire (measure) the electrocardiographic signal having a larger amplitude between the hand and the chest or other suitable location.

According to the present preferred embodiment, when the user holds the grip-type electrocardiographic measuring device 1 with both hands, the finger (e.g., the index finger and/or the middle finger) of the one hand makes contact with the first electrocardiographic electrode 19A disposed on the main body portion 10, and the finger (e.g., the thumb and/or the index finger) of the other hand makes contact with the second electrocardiographic electrode 19B disposed on the surface of the flange portion 18. In this case, the position of the thumb of the one hand is restricted by the stopper portion 11 projecting along the axial direction of the main body portion 10, and the plate-shaped flange portion 18 is mounted on the side surface of the main body portion 10 so as to be bendable in the direction (up to an angle) which is orthogonal or substantially orthogonal to the projecting direction of the stopper portion 11, so that both hands are prevented from making contact with each other. That is, it is possible to hold the grip-type electrocardiographic measuring device 1 without causing both hands to make contact therewith. Further, even when the main body portion 10 is miniaturized, it is easily gripped while the fingers of both hands do not interfere with each other. Further, since the fingers of both hands hardly make contact with each other, it is possible to prevent the deterioration in S/N due to contact between the fingers.

In the grip-type electrocardiographic measuring device 1 according to the present preferred embodiment described above, the first electrocardiographic electrode 19A is disposed at the back surface side of the main body portion 10. Alternatively, a first electrocardiographic electrode 19C may be disposed on the recess 17 or a housing surface that is close to the recess 17.

Figure 5:
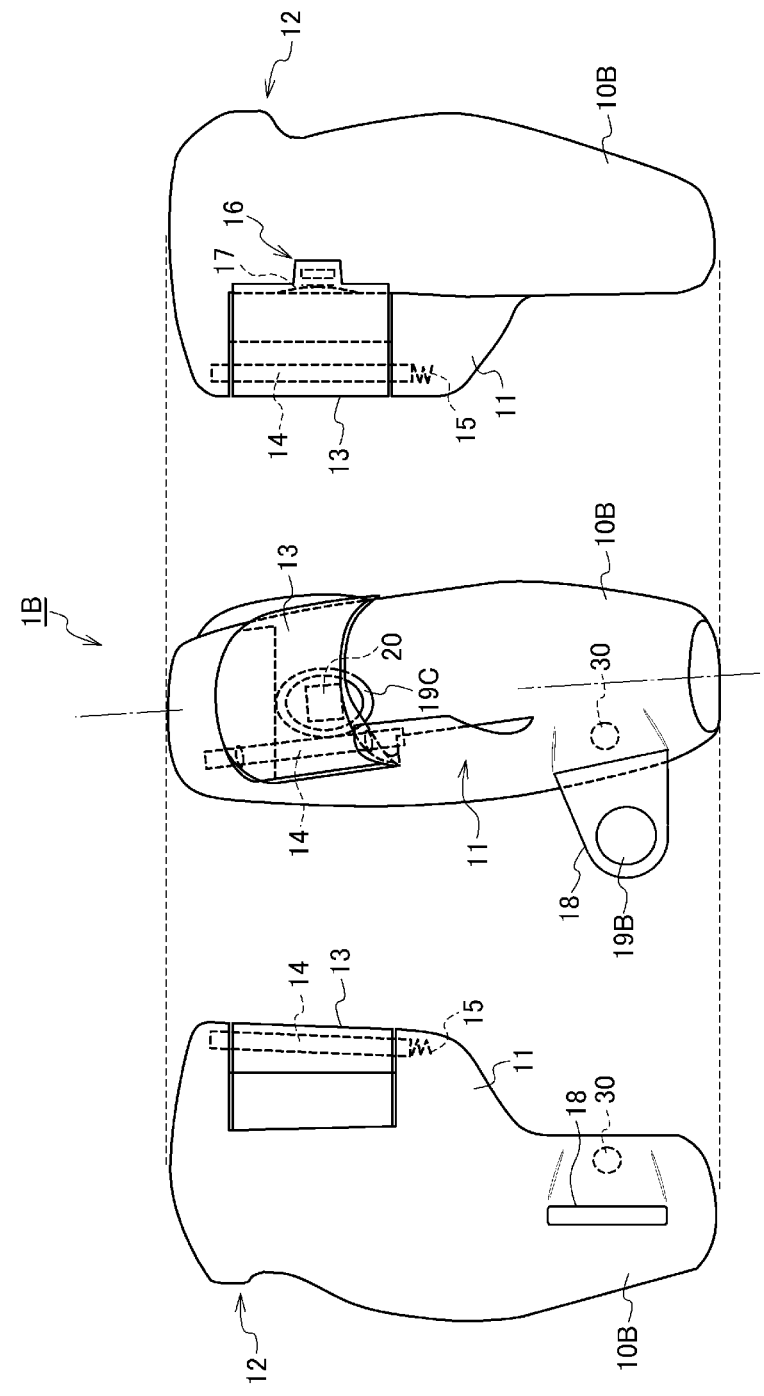
FIG. 5 illustrates a front view and right and left side views (a state in which a flange portion is opened) of a grip-type electrocardiographic measuring device according to a first modification of a preferred embodiment of the present invention.

Next, a grip-type electrocardiographic measuring device 1B according to a first modification of a preferred embodiment of the present invention will be described with reference to FIG. 5. In this case, description of the same or similar components as or to those in the above-described preferred embodiment will be simplified or omitted, and different points will be mainly described. FIG. 5 is a front view and right and left side views (a state in which the flange portion 18 is opened) of the grip-type electrocardiographic measuring device 1B according to the first modification. In FIG. 5, components that are the same as or equivalent to those in the above-described preferred embodiment are denoted by the same reference numerals.

The grip-type electrocardiographic measuring device 1B is different from the grip-type electrocardiographic measuring device 1 according to the above-described preferred embodiment in that the ring-shaped first electrocardiographic electrode 19C is disposed along the outer edge of the recess 17 provided around the photoplethysmographic sensor 20. In other words, the first electrocardiographic electrode 19C is disposed at a position offset from the stopper portion 11 (the swing shaft 14 of the light shielding cover 13) along the peripheral direction of the main body portion 10, and when a user grips the main body portion 10 with one hand (for example, the right hand), the fingertip (inner portion) of the thumb of the one hand restricted by the stopper portion 11 makes contact with the first electrocardiographic electrode 19C.

The remaining configuration is the same as or similar to those of the grip-type electrocardiographic measuring device 1, and detailed description thereof will therefore be omitted here. Note that the first electrocardiographic electrode 19C may be disposed in the recess 17 (i.e., around the photoplethysmographic sensor 20).

In the above-described preferred embodiment, the light shielding cover 13 is swingable (openable and closable). Alternatively, a configuration in which the light shielding cover 13 is fixed, that is, no opening/closing mechanism of the light shielding cover 13 (the swinging shaft 14, the biasing member 15, the locking mechanism 16, for example) is included may be provided.

Figure 6:
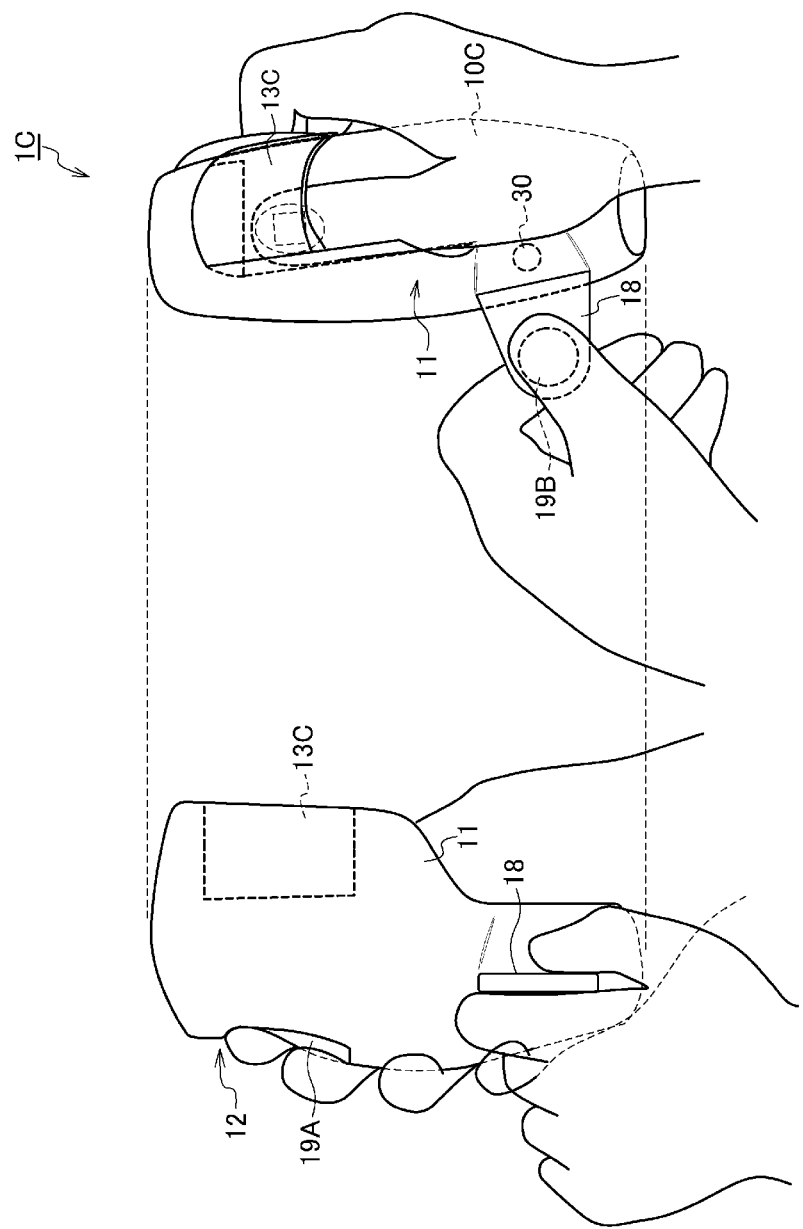
FIG. 6 is a view (a front view and a side view) illustrating a grip-type electrocardiographic measuring device according to a second modification of a preferred embodiment of the present invention and a state (a state in measurement) in which the grip-type electrocardiographic measuring device is gripped by hands.
Figure 7:
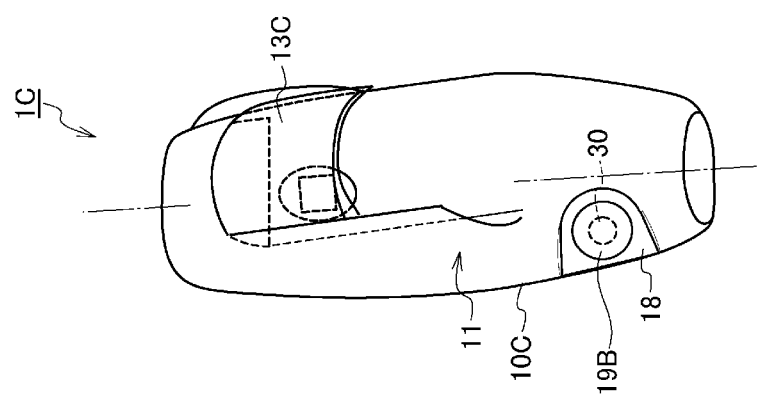
FIG. 7 is a front view (a state in which a flange portion is closed) of the grip-type electrocardiographic measuring device according to the second modification.

Next, a grip-type electrocardiographic measuring device 1C according to a second modification of a preferred embodiment of the present invention will be described with reference to FIGS. 6 and 7. In this case, description of the same or similar components as or to those in the above-described preferred embodiment will be simplified or omitted, and different points will be mainly described. FIG. 6 is a diagram (front view and side view) illustrating the grip-type electrocardiographic measuring device 1C according to the second modification and a state (a state in measurement) in which the grip-type electrocardiographic measuring device 1C is gripped by hands. FIG. 7 is a front view (a state in which the flange portion 18 is closed) of the grip-type electrocardiographic measuring device 1C according to the second modification. In FIGS. 6 and 7, components that are the same as or equivalent to those in the above-described preferred embodiment are denoted by the same reference numerals.

The grip-type electrocardiographic measuring device 1C is different from the above-described grip-type electrocardiographic measuring device 1 in that a light shielding cover 13C is fixed in a closed state (that is, no opening/closing mechanism (the swing shaft 14, the biasing member 15, the lock mechanism 16, and the like) is provided). Note that the light shielding cover 13C has a semi-cylindrical or substantially semi-cylindrical shape and covers an upper portion of the photoplethysmographic sensor 20. The remaining configuration is the same or substantially the same as those of the above-described grip-type electrocardiographic measuring device 1, and detailed description thereof will therefore be omitted here.

According to the second modification, since the light shielding cover 13C includes no movable portion (opening/closing mechanism), it is possible to reduce the weight and cost of the grip-type electrocardiographic measuring device 1C and to improve durability.

While the preferred embodiments of the present invention have been described above, the present invention is not limited to the above-described preferred embodiments, and various modifications may be made. For example, the shape of the grip-type electrocardiographic measuring device 1 (1B or 1C) may be different such that the stopper portion 11 and the flange portion 18 are provided at symmetrical opposite positions for right-hand use and left-hand use.

Further, in the above-described preferred embodiments, the flange portion 18 is bent toward the front side of the main body portion 10 so as to extend along the outer periphery of the main body portion 10. Alternatively, for example, the flange portion 18 may be bent toward the back surface side of the main body portion 10 and fixed along the outer periphery (back surface side) of the main body portion 10. It should be noted that, in such a configuration, in order to prevent the flange portion 18 from hanging down toward the back surface side of the main body portion 10 during measurement, for example, it is preferable to provide a configuration in which a flange stopper to prevent the flange portion 18 from hanging down toward the back surface side of the main body portion 10 is able to be pulled in and out in the back surface of a connecting portion between the flange portion 18 and the main body portion 10.

Further, in the above-described preferred embodiments, the grip-type electrocardiographic measuring device 1 (1B or 1C) includes the photoplethysmographic sensor 20. Alternatively, for example, a piezoelectric pulse wave sensor or an oxygen saturation sensor may be provided, instead of the photoplethysmographic sensor 20. Note that the photoplethysmographic sensor 20, the light shielding cover 13, and the step 12 are not essential and may be omitted.

In the above-described preferred embodiments, pieces of information (measurement data), such as the photoplethysmographic signal and the pulse rate, which have been detected or measured, are transmitted to the external device by the wireless communication module 60. Alternatively, the pieces of acquired information (measurement data) may be stored in a memory in the device during measurement, and the device may be connected to the external device and the pieces of information may be transferred thereto after the measurement is finished.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. An electrocardiographic measuring device comprising:
    a grippable main body portion having a spheroid or substantially spheroid shape;
    a plate-shaped flange portion mounted on a side surface of the main body portion;
    a first electrocardiographic electrode disposed on the main body portion and is configured to make contact with a first hand when the main body portion is gripped by the first hand; and
    a second electrocardiographic electrode disposed on a surface of the flange portion and making contact with a finger of a second hand when the flange portion is pinched by the second hand; wherein
    the flange portion is configured to be bent from a mounting portion on the main body portion.

2. The electrocardiographic measuring device according to claim 1, further comprising a stopper mechanism to prevent the flange portion from hanging down toward a back surface side of the main body portion during measurement.

3. The electrocardiographic measuring device according to claim 1, further comprising a fixing mechanism that fixes the flange portion along an outer peripheral surface of the main body portion.

4. The electrocardiographic measuring device according to claim 3, wherein the second electrocardiographic electrode is disposed on the flange portion so as to be exposed to an outer surface of the flange portion in a state in which the flange portion is fixed along the outer peripheral surface of the main body portion.

5. The electrocardiographic measuring device according to claim 1, further comprising:
    a stopper portion projecting along an axial direction of the main body portion and abutting against a side surface of a thumb of one of the first and second hands to restrict a position of the thumb when a user grips the main body portion by the first hand; wherein
    the flange portion is mounted to be bendable in a direction which is orthogonal or substantially orthogonal to a projecting direction of the stopper portion.

6. The electrocardiographic measuring device according to claim 1, wherein the flange portion is made of a material that is the same as material from which the second electrocardiographic electrode is made.

7. The electrocardiographic measuring device according to claim 1, wherein a thickness of an outer edge of the flange portion is larger than a thickness of a central portion of the flange.

8. The electrocardiographic measuring device according to claim 3, wherein the fixing mechanism includes a magnet.

9. The electrocardiographic measuring device according to claim 3, wherein the fixing mechanism includes a recess in the flange portion and a protrusion provided on the main body portion so as to be fitted into the recess.

10. The electrocardiographic measuring device according to claim 1, wherein a concave portion is provided in an area of an outer peripheral surface of the main body portion, and the flange portion is configured to be housed in the concave portion.

11. The electrocardiographic measuring device according to claim 1, wherein the flange portion includes two films having different lengths that are bonded to each other at ends thereof.

12. The electrocardiographic measuring device according to claim 1, wherein the first electrocardiographic electrode and the second electrocardiographic electrodes are each made of at least one of stainless steel, titanium, Au, conductive gel, conductive rubber, or conductive cloth.

13. The electrocardiographic measuring device according to claim 1, further comprising a photoplethysmographic sensor disposed on the main body portion.

14. The electrocardiographic measuring device according to claim 13, further comprising a light shielding cover provided on the main body portion to prevent disturbance light from entering the photoplethysmographic sensor.

15. The electrocardiographic measuring device according to claim 14, wherein the light shielding cover has a semi-cylindrical or substantially semi-cylindrical shape to cover a thumb during measurement.

16. The electrocardiographic measuring device according to claim 14, wherein the light shielding cover is mounted on the main body portion to be swingable about a swing shaft provided in parallel or substantially in parallel to an axial direction of the main body portion.

17. The electrocardiographic measuring device according to claim 16, wherein the swing shaft includes a biasing member to bias the light shielding cover in an open direction.

\* \* \* \* \*